United States Patent [19]

Tsukagoshi et al.

[11] Patent Number: 5,266,199
[45] Date of Patent: Nov. 30, 1993

[54] SERUM SEPARATING APPARATUS

[75] Inventors: Youichi Tsukagoshi, Tokyo; Toshio Inoue, Sakura; Toshimasa Yamamoto, Kawasaki, all of Japan

[73] Assignee: Nigata Chemicals and Plastics Co., Ltd., Yokohama, Japan

[21] Appl. No.: 795,199

[22] Filed: Nov. 19, 1991

[30] Foreign Application Priority Data

Nov. 20, 1990 [JP] Japan ............................ 2-314698
Jan. 11, 1991 [JP] Japan ............................ 3-013994

[51] Int. Cl.⁵ ................................................ B01D 21/26
[52] U.S. Cl. ................................. 210/516; 210/514; 210/518; 422/102; 422/103
[58] Field of Search .............. 210/514, 512.1, 515, 210/782, 516, 518; 422/101, 102, 103; 99/458; 137/172

[56] References Cited

U.S. PATENT DOCUMENTS

| 1,859,362 | 5/1932 | Grauman | 210/514 |
| 3,780,935 | 12/1973 | Lukacs et al. | 210/782 |
| 3,814,248 | 6/1974 | Lawhead | 210/516 |
| 3,897,343 | 7/1975 | Ayres | 210/516 |
| 4,055,501 | 10/1977 | Cornell | 210/516 |
| 4,189,385 | 2/1980 | Greenspan | 210/518 |
| 4,464,254 | 8/1984 | Dojki et al. | 210/516 |

FOREIGN PATENT DOCUMENTS

| 56-118669 | 9/1981 | Japan . |
| 57-54861 | 4/1982 | Japan . |
| 1-28346 | 6/1989 | Japan . |

*Primary Examiner*—Robert A. Dawson
*Assistant Examiner*—Sun Uk Kim
*Attorney, Agent, or Firm*—Hoffmann & Baron

[57] ABSTRACT

This invention relates to an apparatus used in a centrifugal separating step for sample preparation in the field of clinical chemistry. Especially, the invention relates to a separating apparatus used for isolating a serum fraction from a freshly isolated blood sample without contamination with a clot fraction. A serum separating apparatus according to the present invention is characterized by comprising an elastic body in the form of a cylindrical tube and a ball which can fitted to an opening of the elastic body and by positioning at a boundary of said fractions after the centrifugation.

19 Claims, 6 Drawing Sheets

SERUM SEPARATING APPARATUS

BACKGROUND OF THE INVENTION

1. Field of the Invention

This invention relates to an apparatus used in a centrifugal separating step for sample preparation in the field of clinical chemistry. Especially, the invention relates to a separating apparatus used for isolating a serum fraction from a freshly isolated blood sample without contamination with a clot fraction.

2. Description of the Prior Art

It has been known that diagnostic tests, especially the diagnostic tests for blood samples are essential in the field of clinical diagnosis, because blood contains essential components for maintaining biological conditions of the body. Such components are blood cells, enzymes, hormones, proteins, sugars and the like, and they mirror the disturbances of the normal working of the body.

In recent years, various kinds of diagnostic tests of blood samples have been developed and used in the field of clinical chemistry. With the advance in diagnostic tests, hospital biochemists and their coworkers have been faced with increasing demands for specialized tasks for testing blood samples. In addition, they also have been faced with increasing demands for routine tasks such as sample preparations for the specialized tests. To meet the demands of these tests, equipment for automatically testing the samples have been developed and provided to hospitals and laboratories. While these analyzers have increased the efficiency of performing the necessary tests, a problem has remained in finding ways and means of isolating a serum fraction without contamination with a clot fraction for supplying the isolated serum for clinical analyses.

Although most of the diagnostic blood tests include a step of separating blood into serum and clot fractions by means of centrifugal separation, it is difficult to prepare a serum fraction quickly and effectively from the blood sample because at least a part of a pellet containing blood cells come off the wall of the tube and spreads out freely in the serum. Therefore, it has been required to carefully handle the centrifuged sample in the tube.

To solve this problem, various types of serum separating methods have been suggested.

One type of the such methods comprises a step of using a device incorporating a chemical substance called a sealant. This sealant is characterized by thixotropic, water insoluble, and substantially non-toxic properties. For example, Michel J. Lukacs and et al., U.S. Pat. No. 3,780,935 issued Dec. 25, 1973, discloses a sealant having a proper specific gravity to divide serum and clot fractions. This sealant comprises essentially of a silicone fluid and an inert filler such as silica dispersed therein. The blood separation using this sealant is accomplished by inserting a device containing a supply of the sealant into a container such as a glass tube holding a sample of blood. In addition, the above device is characterized by a nozzle portion which extends into the sample. During the centrifugation, the device discharges the sealant into the blood. After the centrifugation, the sealant is migrated to a boundary of the two fractions.

Another type of the serum separating methods comprises a step of using a porous plug. For example, Japanese patent application (TOKKYO KOHO number HEI-1-28346) discloses the insertion plug in the shape of a column or a conical frustum, which is made of a multi-porous material and the bottom of the plug is covered with a rigid plate. After the centrifugation, the insertion plug is migrated to a boundary of the two fractions to separate them each other.

However, these conventional devices have some difficulties in fractionation of the blood sample. That is, in the case of the blood fractionation procedure using a high molecular substance such as silicone as a sealant, it is difficult to separate this sealant with the blood fraction. In addition, the physiological or chemical nature of the blood will be changed by adding the sealant. In the case of using the device comprising a multi-porous material, the pores are often plugged with the clot and incomplete fractionation of the blood results.

Furthermore, other types of blood separating means have been proposed. For example, Japanese patent application No SHO-55-130519 discloses a separating device in the form of a frustoconical cylinder having a narrow opening at the top portions thereof to pass serum through the device and projected portions on the side wall thereof to contact with the inner surface of the tube. This device is inserted into the tube after the clot is formed by the agglutination in the tube. However, the time is wasted in waiting to complete the clot-forming process.

Still furthermore, another Japanese patent application (TOKKYO KOHO SHO-56-118669) discloses a separating apparatuses comprising a frustoconical plug and a ring. This ring is slipped on the frustoconical plug by the centrifugal force to separate the serum and clot fractions. However, if the plug is misaligned, the plug does not fit into the ring.

It is noted that the above documents do not disclose how to fit the device to different types of tubes, glass tubes and plastic tubes, which are widely used for general blood separating procedures.

In general, two types of tubes are used for general blood separating procedures. That is, one type of the tube is made of a glass and the other type of the tube is made of a plastic material. The glass tube has a constant or a slightly varying inner diameter, while the plastic tube has a gradient of inner diameter. For example, inner diameters of each portion of a plastic tube (10 ml vol.) are varied from 14.0 mm to 13.0 mm.

Accordingly, it is evident that two types of the serum separating apparatuses must be provided to fit to the different types of the tubes. It is required that when the serum separating apparatus is moved smoothly along an inner surface of the plastic tube during the centrifugation, the device diameter must be changed to fit to the variation of the inner diameters of the tube.

However, the above references do not show any means to solve this problem.

SUMMARY OF THE INVENTION

Accordingly, one of the objects of the present invention is to provide a blood separating apparatus which can be easily attached and detached in a tube and also can be handled easily during the blood separating procedure to isolate serum without any clot contamination.

Another important object of this invention is to provide a blood separating apparatus characterized by using a high molecular material with non-thrombotic and biologically inactive properties.

It is a further object of this invention is to provide a blood separating device having a structure which is able to change its outlet diameter to fit to the variation of the inner diameter of the tube.

The present invention relates to a separating apparatus used for isolating a serum fraction from a freshly isolated blood sample without contaminating the clot fraction. The serum separating apparatus to be equipped in a blood sampling tube according to an embodiment of the present invention is characterized by comprising a cylindrical elastic body and a ball which can be fitted to an opening of said cylindrical elastic body. The serum separating apparatus according to another embodiment of the present invention is characterized by further comprising an elastic ring which is responsible for adapting to a gradient of the inner diameter of a plastic tube. The blood separating apparatus according to the present invention may be easily attached and detached in a tube and also can be handled easily during the blood separating procedure to isolate serum without any clot contamination. Also, the outlet diameter of the above apparatuses may be changed during travel along the inner surface of the tube to fit.

BRIEF DESCRIPTION OF THE DRAWINGS

Further objects and advantages of the present invention will be apparent from the following description, reference being had to the accompanying drawing wherein preferred embodiments of the present invention are clearly shown.

DETAILED DESCRIPTION OF THE INVENTION

Figure 1:
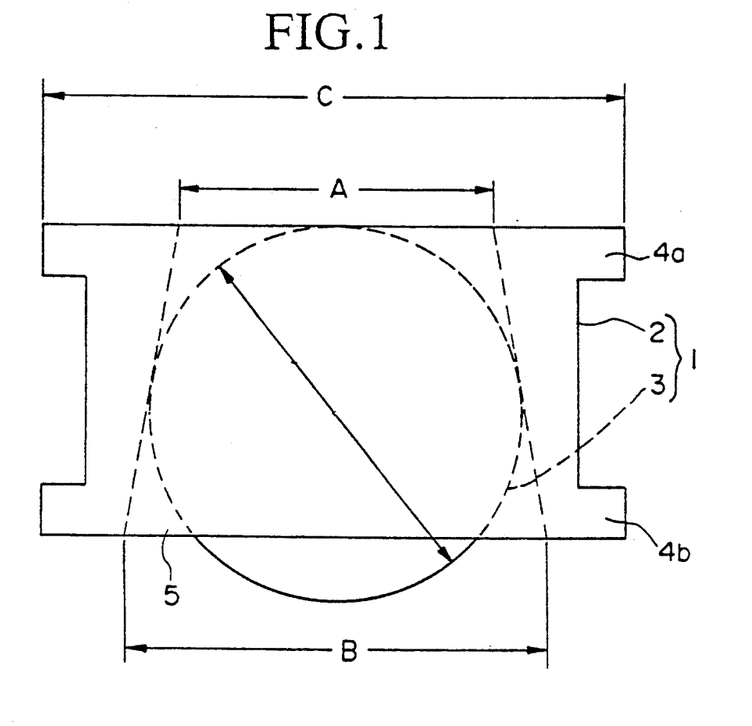
FIG. 1 is a side elevational view of a first embodiment of the present invention.
Figure 2:
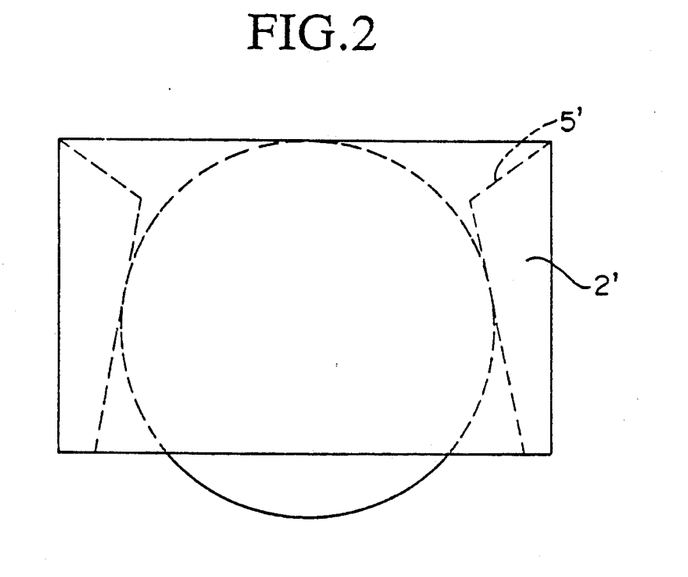
FIG. 2 is a side elevational view of a modified first embodiment of the present invention.

FIGS. 1 and 2 show one of the first preferred embodiment of the present invention.

In FIG. 1, numeral 1 indicates a serum separating apparatus comprising an elastic body 2 and a ball 3.

The elastic body 2 is made of non-thrombotic and biologically inactive material which is difficult to be adhered by the blood composition, for example semi-hardening or hardening type of plastics of specific gravity more than 1.03, preferably in the range of 1.05-1.5, which is selected from a group of ABS resin, polyethylene terephtalate resin, polyurethane resin, polybuthylene terephtalate resin, polycarbonate resin, polyamide resin, polymethylmethacrylate resin, polyacetal resin, and the like. Also, the elastic body 2 is formed as a cylindrical tube having top and bottom elastic flanges 4a and 4b both being horizontally projected from the surface of the tube and having an opening 5 throughout one end to another with a gradient of inner diameters along the longitudinal axis of the body 2 so as to form a tapered inside wall.

It is preferably that the height of the elastic body is 3 mm or over, more preferably in the range of 5-10 mm, because of moving smoothly along an inside of the tube.

As indicated by a dotted line in FIG. 1, an opening 5 is the inner space of the elastic body 2 and has the shape such as a frustum cone being concentric with a central axis of the body 2. For the purpose of holding the ball 3 by the opening 5 after the centrifugation, an inner diameter of the top portion (A) of the opening 5 is smaller than that of the bottom portion (B) and a diameter of the ball 3.

The above ball 3 is made of a material of specific gravity lower than that of the blood sample (1.05-1.06), for example a plastic material such as polystyrene, polyethylene, polypropylene or the like. This ball 3 can be fitted in an opening 5 of the elastic body 2. It is preferable that a diameter of the ball is in the range of 35% or more of the inner diameter of the tube and preferably in the range of 50-90% thereof to maintain suitable migration in the tube comprising blood.

As shown in FIG. 2, it is preferable that the upper end of the opening 5' is widely opened to prevent accumulation of clot or platelet adhesion on the elastic body 2'. In addition, in the case of using glass tube of constant inner diameter, the above described flanges 4a and 4b can be excluded.

A preferable serum separation method using the above preferable device according to the present invention comprises steps of: (1) preparing a blood sample from an animal body; (2) centrifuging the tube with the blood sample at 1200 G; and (3) isolating the serum fraction from the tube.

FIGS. 7a-d are diagrams for assist in explaining the method using the apparatus according to the present invention.

Figure 7A:
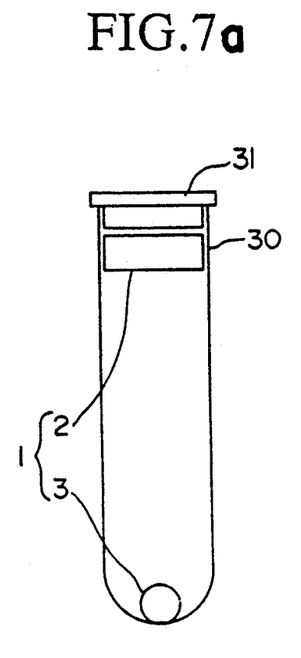
FIG. 7a-7d are diagrams of assistance in explaining the method using the apparatus according to the present invention.

Before the tests, a serum separation apparatus is equipped in a tube 30 with a lid 31. As shown in FIG. 7a, it is preferable to put the elastic body 2 in a position of the tube just below the lid 31.

Figure 7B:
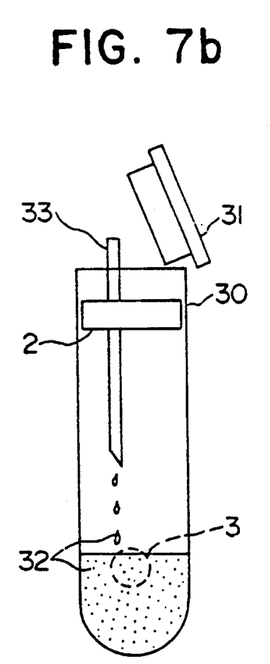
Figure 7C:
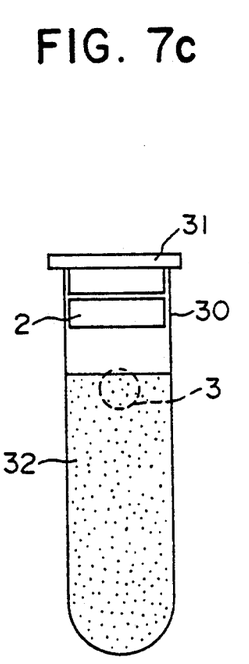

First, a required volume of blood is collected from an individual by a syringe to prepare a blood sample 32, and subsequently the blood sample 32 is poured into the tube 30 (FIG. 7b). That is, the blood sample 32 is poured into the tube by passing a needle 33 of the syringe through the opening 5 of the body 2. Thus the ball 3 is floated on blood 32 and is located remote from the body 2.

Figure 7D:
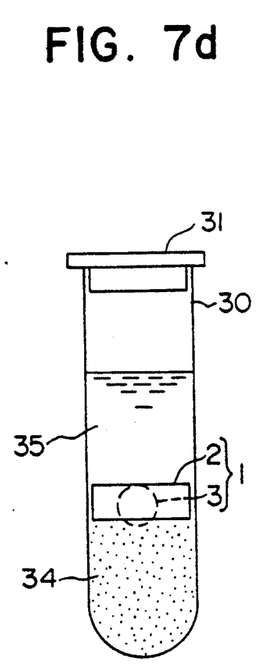

Second, the tube 30 is subjected to a step of centrifugation. During the centrifugation, as shown in FIG. 7d, a centrifugal force is applied from the top to the bottom of the tube 30 along its longitudinal direction, and simultaneously blood cells, the elastic body 2 and the ball 3 are migrated to the bottom of the tube at different speeds, respectively.

At the beginning of the centrifugation, a ball 3 is buried in blood cells which is being deposited. After that, the clot portion 34 is gradually formed and at the same time the ball 3 is gradually passed up to the top of the clot portion 34. On the other hand, the elastic body 2 is gradually migrated downward. Eventually, the clot portion 34 and serum portion 35 are perfectly divided and then the ball 3 on the clot portion 34 is fit to the opening 5 of the body 2 at a boundary between the serum and clot portions.

After the centrifugation, the serum fraction 35 may be isolated by using a syringe or pipette or by an aspiration or decantation, while the clot fraction is remained at a bottom of the tube.

Figure 3:
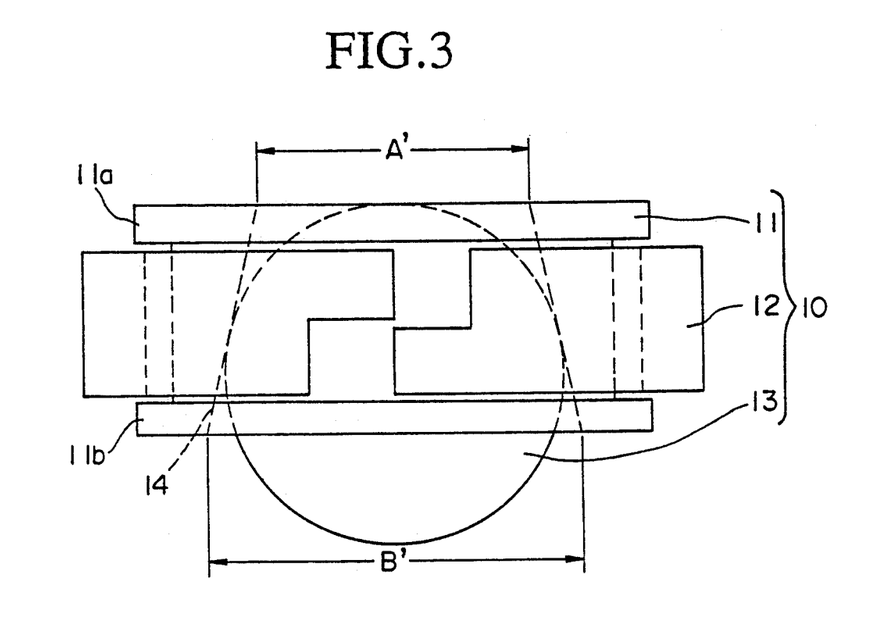
FIG. 3 is a side elevational view of a second embodiment of the present invention.
Figure 4:
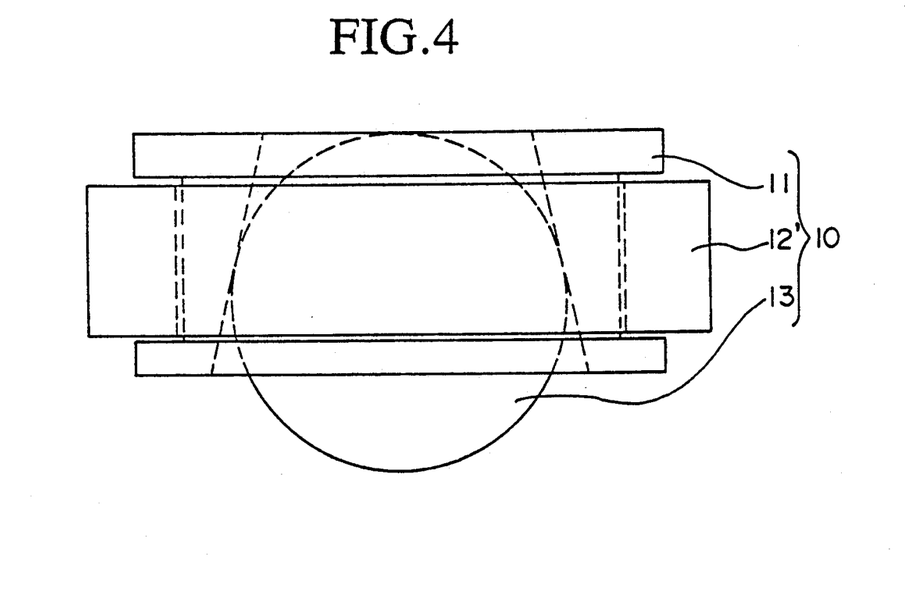
FIG. 4 is a side elevational view of a modified second embodiment of the present invention.

FIG. 3 and 4 show another preferred embodiment of the present invention.

In FIG. 3, numeral 10 indicates a serum separating apparatus comprising an elastic body 11, an elastic ring 12 and a ball 13. This ball 13 can be fitted in an opening 14 of the elastic body 11. The elastic body 11 and the ball are almost the same as those in FIG. 1.

The elastic ring 12 is also made of non-thrombotic and biologically inactive material which is difficult to be adhered by the blood composition, such as a semi-hardening or hardening type of plastics of specific gravity more than 1.03, preferably in the range of 1.05–1.5, which is selected from a group of ABS resin, polyethylene terephtalate resin, polyurethane resin, polybuthylene terephtalate resin, polycarbonate resin, polyamide resin, polymethylmethacrylate resin, polyacetal resin, and the like.

The elastic ring 12 is made of a thin plate which is formed as a ring with a part cut off. Therefore the elastic ring 12 has a shape such as a circular arc having two free-ends so as to being flexible in a radius direction of the ring to fit to an inner surface of the plastic tube. It is preferable that two ends of the plate 12 are separated and formed as L-shape and reversed L-shape, respectively, so as to meet each other.

When the above apparatus is inserted in a plastic tube, a peripheral surface of the elastic ring 12 is slidably supported within the tube by the action of the elastic force of the ring. During the centrifugation, the elastic ring 12 moves down within the tube and a distance between the above ends of the elastic ring 12 approach each other to change the ring diameter because an inner diameter of the lower portion of the plastic tube is smaller than that of the upper portion and thus the elastic force of the ring acts on the wall of the tube and the wall pushes the ring against the force. On the other hand, when the elastic ring 12 moves up, the distance between the above ends is extended.

Furthermore, the ring is concentrically provided with the elastic body 11 so as to cover the surface of the body 11 between the flanges 11a and 11b. In addition, these flanges 11a and 11b act as a means for holding the ring 12 to avoid slipping out the position.

It is noted that materials for making the elastic ring 12 are not limited to the above materials. As shown in FIG. 4, for example, it is possible to make an elastic ring as a closed circle 12' by processing fiber materials selected from metal materials such as stainless fibers, inorganic materials such as glass fibers, or plant materials such as cellulose fibers, animal materials such as silk fibers or mixtures thereof. In this case, it is preferable that a blood aggregation accelerating agent such as a $SiO_2$ powder may be comprised in the elastic ring so as to keep a serum fraction away from a clot fraction after the centrifugation.

Figure 5:
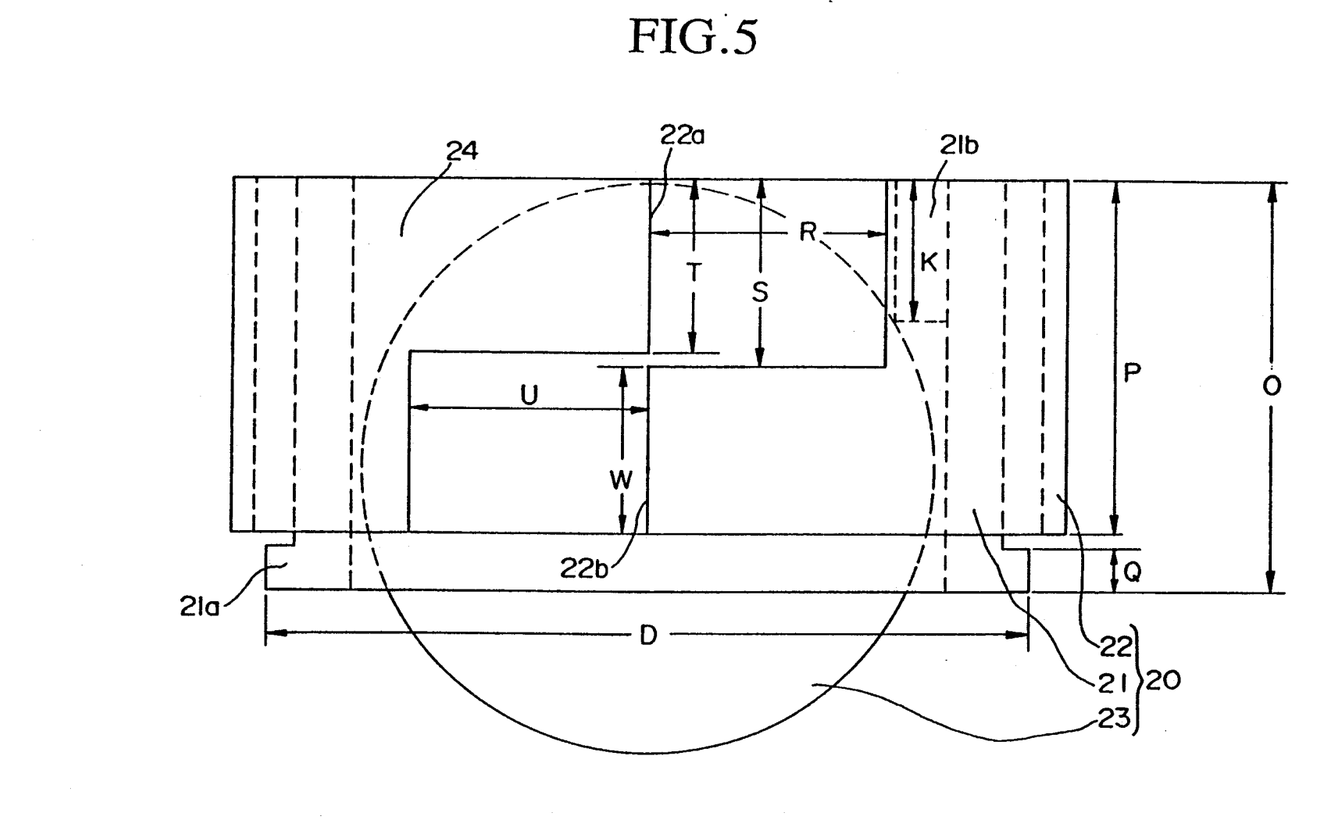
FIG. 5 is a side elevational view of a third embodiment of the present invention.
Figure 6:
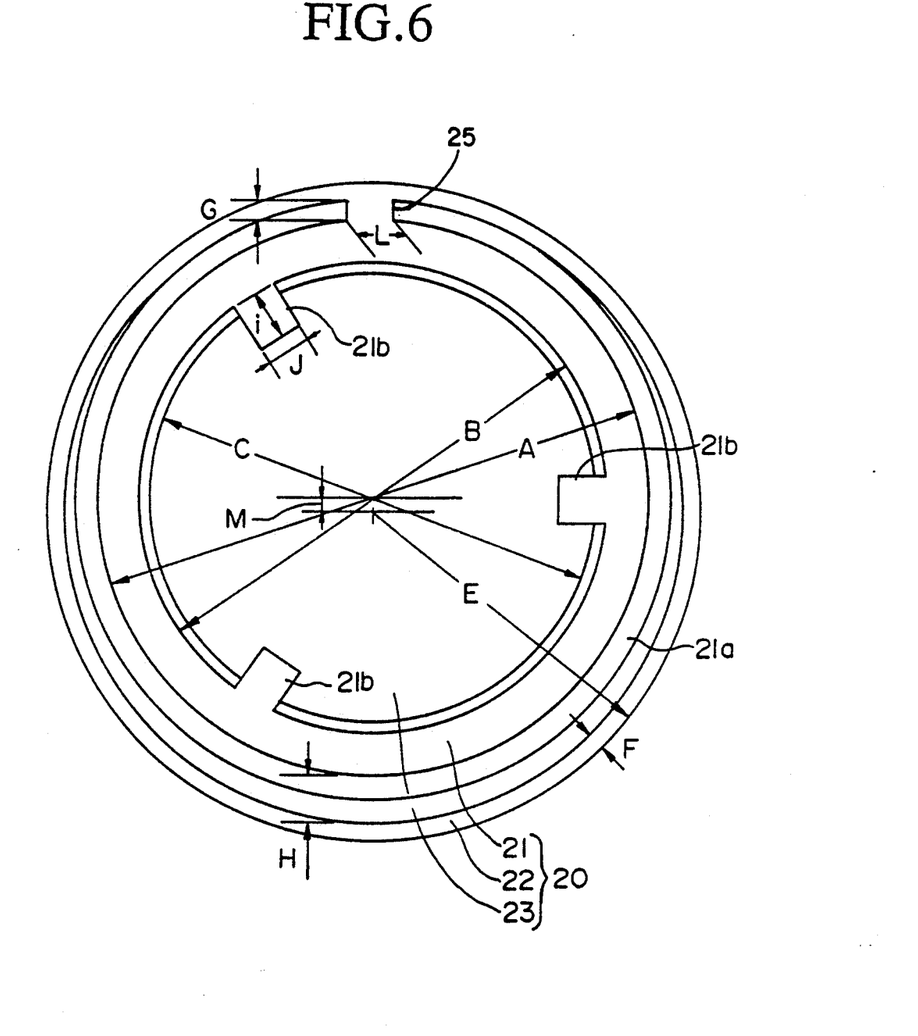
FIG. 6 is an elevational view of a third embodiment of the present invention.

FIGS. 5 and 6 show further preferred embodiment of the present invention.

In this figure, numeral 20 indicates a serum separating device comprising an elastic body 21, an elastic ring 22 and a ball 23. This ball 23 can be fitted in an opening 24 of the elastic body 21.

In this embodiment, the elastic ring 22 is made of a thin plate which is formed as a ring with a part cut off. Therefore the elastic ring 22 has a shape such as a circular arc having two free-ends so as to be flexible in a radius direction of the ring to fit to an inner surface of the plastic tube.

The elastic body 21 is formed as a cylindrical tube and the body 21 is provided within an inner space of the elastic ring 22. As shown in FIG. 6, a part of the elastic ring is fixed with a part of the elastic body 21 by means of a supporting entity 25. The upper inner side of the elastic body 21 has three projected portions 21b which is extended horizontally to prevent passing the ball 23 through the body. On the other hand, the bottom of the elastic body 21 has an elastic flange 21a horizontally projected to support the elastic ring 22.

It is noted that the blood separating apparatus can be used in a vacuum blood container. In this case, a serum separating apparatus is settled in the container just below its cap and a blood sample is injected into the container without removing the cap.

It is desirable to coat the above describe parts of the serum separating apparatus with anti-adhesive or ant-clotting agent because it is difficult to avoid adhering or attaching blood cells on the apparatus. In this case, a preferable coating material is selected from a group of silicon resin, silicon oil, fluoroplastics and the like. Also, a preferable anti-coagulating agent is a heparin.

If the sample is to be subjected to glucose analysis, it is preferable that an anti-glycolysis agent such as sodium fluoride, mono-iodinic sodium acetate or the like is coated on a surface of the serum separating apparatus because glucose comprised in the serum fraction is easily glycolysed by cells in the clot fraction.

Furthermore, it is possible to put a small amount of conventional sealant in a gap between the elastic ring and body to avoid having cells or the like enter into the serum fraction. Also, it is preferable that the sealant is plugged into a space between the two ends of the elastic ring.

EXAMPLES

Example 1

The serum separating device according to the present invention as shown in FIG. 1, except of that the flanges are extruded, was manufactured.

In this example, the serum separating device has a weight of 1.019 g and an average density of 1.05 g/cm$^3$, and this device consists of an elastic body and a ball.

The elastic body (0.59 g weight) was made of silicone rubber having a density of 1.16 g/cm$^3$ and a hardness of 55, and also the elastic body was formed into a cylindrical shape having following dimensions i.e., an inner diameter of the top end (A) is 9.2 mm; and inner diameter of the base end (B) is 10.8 mm; an outer diameter (C) is 13.2 mm; and a height of the body is 8.7 mm.

The ball having a diameter of 9.65 mm and a weight of 0.429 g was used. This ball was made of a high density polyethylene having a density of 0.96 g/cm$^3$ ("JU 080", Mitubishi Kasei Co., LTD.).

Figure 8A:
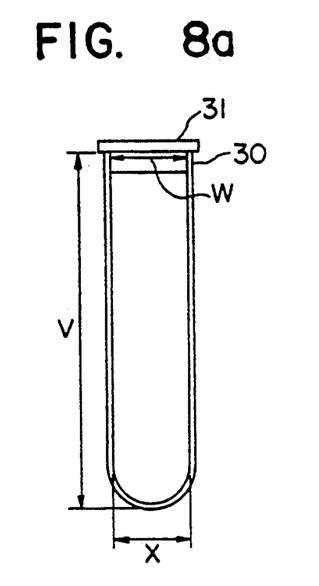
FIG. 8a is a side elevational view of a glass tube used in the present invention, it being broken away for clearness.

As shown in FIG. 8a, all of the tubes 30 used in this example were commercially obtainable glass tubes (10 ml vol., "VENOJECT" evacuated blood-collecting tube; code No. BT-100P, TERUMO Co., Ltd.) with a lid 31, which are generally used for the blood test. These tubes 30 have dimensions: 99 mm of a total length (V); 13.25–13.50 of inner diameter at the top end (W); and 13.55–13.60 mm of inner diameter at the other portions except of the bottom (W).

A blood fractionation using the above device was performed as follows.

In the first step, by means of a syringe, 7 ml of blood introduced in each tube of a group consisting of ten tubes in which five tubes of them were equipped with the serum separating devices and the others were not.

In the case of the tube with the device, blood was introduced through the opening of the elastic body to the bottom of the tube, following that the tubes were settled down for 1.5 hour to aggregate the blood.

In the second step, these tubes having blood samples were Centrifuged at 3,000 r.p.m. (approximately 1200 G) for 10 minutes at 20° C. to separate serum and clot fractions.

After the centrifugation, localization of the serum separating device was observed, resulting that the ball was perfectly fit to the opening of the elastic body and they were located between the serum and clot fractions. In addition, a part of the clot portion was not attached or adhered on the ball and the serum separating device. It is noted that the serum fraction can be easily isolated without any contamination in spite of isolating the fraction by inclining the tube in a gentle manner.

Isolated serum fraction was subjected to chemical analysis by means of the automatic blood analyzer (HITACHI 736-60E type, Hitachi Sisakusyo Co., Ltd.). That is, a detailed analysis of each sample was performed as quantitative determination of following substances and items: lactic acid dehydrogenase (LDH, I.U); creatine phosphokinase (CPK, I.U); glutamic oxaloacetic transaminase (GOT, I.U); glutamic pyruvic transaminase (GPT, I.U); alkaline phosphatase (ALP, I.U); leucine aminopeptidase (LAP, U/dl); gamma-glutamiltranspeptitase ($\gamma$-GTP, I.U); cholinesterase (ChE); lipoprotein ($\beta$-LP, mg/dl); phospholipid (PL, mg/dl); nonesterified fatty acid (NEFA, mEq/l); urea (UA, mg/l); total cholesterol (T-CHO, mg/dl); free cholesterol (F-CHO, mg/dl); glucose (GLU, mg/dl); magnesium (Mg, mEq/l); inorganic phosphorus (IP, mg/dl); calcium (Ca, mg/dl); blood urea nitrogen (BUN, mg/dl); triacylglyceride (TG, mg/dl); creatinine (CRE, mg/dl); amylase (AMY, I.U); serum total protein (TP, g/dl); albumin (Alb, g/dl); total bilirubin (T.Bil, mg/dl); direct bilirubin (D.bil, mg/dl); sodium (Na, mEq/l); potassium (K, mEq/l); chlorine (Cl, mEq/l); thymol turbidity test (TTT); and zinc sulfate turbidity test (ZTT). The results were listed in Table 1 below. In this table, "+"means that the serum separating apparatus according to the present invention was used and "−" means that serum separating apparatus according to the present invention was not used.

From the results shown in Table 1, the blood separating device according to the present invention does not affect the results of the blood test.

TABLE 1

The values of the chemical analysis of blood samples for clinical diagnosis.

| sample No. | items | the values of chemical analysis. − | + |
|---|---|---|---|
| 1 | LDH | 286 | 284 |
| 2 | | 366 | 368 |
| 3 | | 342 | 340 |
| 4 | | 285 | 285 |
| 5 | | 308 | 303 |
| 1 | CPK | 74 | 72 |
| 2 | | 122 | 124 |
| 3 | | 63 | 67 |
| 4 | | 95 | 94 |
| 5 | | 47 | 47 |
| 1 | GOT | 13 | 14 |
| 2 | | 26 | 25 |
| 3 | | 23 | 24 |
| 4 | | 16 | 17 |
| 5 | | 23 | 22 |
| 1 | GPT | 14 | 13 |
| 2 | | 23 | 23 |
| 3 | | 34 | 34 |
| 4 | | 18 | 18 |
| 5 | | 25 | 25 |
| 1 | ALP | 156 | 158 |
| 2 | | 138 | 139 |
| 3 | | 208 | 218 |
| 4 | | 153 | 155 |
| 5 | | 202 | 204 |
| 1 | LAP | 35 | 35 |
| 2 | | 39 | 39 |
| 3 | | 39 | 38 |
| 4 | | 33 | 34 |
| 5 | | 44 | 44 |
| 1 | $\gamma$-GTP | 16 | 15 |
| 2 | | 12 | 12 |
| 3 | | 12 | 11 |
| 4 | | 7 | 7 |
| 5 | | 13 | 13 |
| 1 | ChE | 9.3 | 9.4 |
| 2 | | 6.4 | 6.3 |
| 3 | | 5.5 | 5.5 |
| 4 | | 7.9 | 8.0 |
| 5 | | 6.8 | 6.8 |
| 1 | TTT | 0.9 | 0.9 |
| 2 | | 0.8 | 0.8 |
| 3 | | 0.7 | 0.7 |
| 4 | | 0.8 | 0.8 |
| 5 | | 0.7 | 0.7 |
| 1 | ZTT | 2.5 | 2.4 |
| 2 | | 3.9 | 3.8 |
| 3 | | 3.2 | 3.1 |
| 4 | | 4.9 | 4.9 |
| 5 | | 3.9 | 4.1 |
| 1 | $\beta$-LP | 596 | 594 |
| 2 | | 377 | 376 |
| 3 | | 291 | 290 |
| 4 | | 233 | 238 |
| 5 | | 326 | 330 |
| 1 | PL | 249 | 255 |
| 2 | | 205 | 202 |
| 3 | | 214 | 213 |
| 4 | | 193 | 195 |
| 5 | | 206 | 202 |
| 1 | NEFA | 0.66 | 0.62 |
| 2 | | 0.66 | 0.67 |
| 3 | | 0.42 | 0.43 |
| 4 | | 0.20 | 0.17 |
| 5 | | 0.37 | 0.35 |
| 1 | UA | 6.0 | 5.9 |
| 2 | | 6.4 | 6.4 |
| 3 | | 5.5 | 5.6 |
| 4 | | 5.1 | 5.1 |
| 5 | | 6.8 | 6.8 |
| 1 | T-CHO | 236 | 238 |
| 2 | | 191 | 191 |
| 3 | | 183 | 187 |
| 4 | | 161 | 162 |
| 5 | | 162 | 170 |
| 1 | F-CHO | 62 | 63 |
| 2 | | 46 | 46 |
| 3 | | 46 | 47 |
| 4 | | 39 | 39 |
| 5 | | 40 | 40 |
| 1 | GLU | 80 | 79 |
| 2 | | 83 | 82 |
| 3 | | 79 | 80 |
| 4 | | 82 | 80 |
| 5 | | 82 | 83 |
| 1 | Mg | 2.1 | 2.1 |
| 2 | | 2.3 | 2.2 |

TABLE 1-continued

The values of the chemical analysis of blood samples for clinical diagnosis.

| sample No. | items | the values of chemical analysis. | |
|---|---|---|---|
| | | − | + |
| 3 | | 2.1 | 2.2 |
| 4 | | 2.1 | 2.2 |
| 5 | | 2.1 | 2.2 |
| 1 | IP | 3.1 | 3.0 |
| 2 | | 3.7 | 3.6 |
| 3 | | 3.4 | 3.3 |
| 4 | | 3.6 | 3.5 |
| 5 | | 3.2 | 3.2 |
| 1 | Ca | 9.5 | 9.6 |
| 2 | | 9.6 | 9.7 |
| 3 | | 9.3 | 9.3 |
| 4 | | 9.7 | 9.7 |
| 5 | | 10.1 | 10.0 |
| 1 | BUN | 15 | 14 |
| 2 | | 18 | 19 |
| 3 | | 12 | 12 |
| 4 | | 12 | 12 |
| 5 | | 11 | 11 |
| 1 | TG | 251 | 250 |
| 2 | | 92 | 91 |
| 3 | | 70 | 71 |
| 4 | | 56 | 57 |
| 5 | | 123 | 125 |
| 1 | CRE | 1.1 | 1.1 |
| 2 | | 1.0 | 1.0 |
| 3 | | 1.0 | 1.0 |
| 4 | | 0.9 | 0.9 |
| 5 | | 1.0 | 1.1 |
| 1 | AMY | 280 | 276 |
| 2 | | 177 | 177 |
| 3 | | 433 | 430 |
| 4 | | 286 | 277 |
| 5 | | 169 | 159 |
| 1 | TP | 6.8 | 7.0 |
| 2. | | 7.3 | 7.6 |
| 3 | | 6.5 | 6.7 |
| 4 | | 7.4 | 7.5 |
| 5 | | 7.2 | 7.3 |
| 1 | Alb | 4.8 | 4.8 |
| 2 | | 5.0 | 5.0 |
| 3 | | 4.6 | 4.5 |
| 4 | | 5.2 | 5.2 |
| 5 | | 5.0 | 5.0 |
| 1 | T · Bil | 0.5 | 0.5 |
| 2 | | 0.4 | 0.4 |
| 3 | | 0.5 | 0.5 |
| 4 | | 0.8 | 0.8 |
| 5 | | 0.7 | 0.7 |
| 1 | D · Bil | 0.1 | 0.2 |
| 2 | | 0.1 | 0.2 |
| 3 | | 0.2 | 0.3 |
| 4 | | 0.3 | 0.2 |
| 5 | | 0.2 | 0.2 |
| 1 | Na | 139 | 140 |
| 2 | | 140 | 140 |
| 3 | | 140 | 140 |
| 4 | | 144 | 143 |
| 5 | | 139 | 139 |
| 1 | K | 4.3 | 4.4 |
| 2 | | 4.6 | 4.5 |
| 3 | | 4.2 | 4.2 |
| 4 | | 4.3 | 4.4 |
| 5 | | 4.0 | 4.0 |
| 1 | Cl | 103 | 105 |
| 2 | | 101 | 102 |
| 3 | | 102 | 102 |
| 4 | | 103 | 103 |
| 5 | | 100 | 100 |

Example 2

The serum separating device according to the present invention comprising an elastic body, an elastic ring and a ball was manufactured as shown in FIG. 5 and 6. In this device 20, the elastic body 21 and the ring 22 were made of ABS resin (transparent grade: CL, specific gravity: 1.10, bending modulus of elasticity: 20,000 kg/cm$^2$, obtained from Denki Kagaku Kogyo Co., Ltd). Also, the ball 23 was made of butadiene-immersed polystyrene material (1.01 of a specific gravity, Ashashi Kasei Kogyo Co., Ltd.), and also it weighs 0.53 g and has an apparent specific gravity of 1.002. A combination of the elastic body 21 and the elastic ring 22 weighs 0.435 g, and also resulting device weighs 0.938 g and a specific gravity of 1.045.

In the figures, each symbol indicates the following dimensions.

"A" indicates an outer diameter of a top portion of the elastic body, 11.7 mm;

"B" indicates an inner diameter of the elastic body, 10.0 mm;

"C" indicates a diameter of the ball, 9.8 mm;

"D" indicates an outer diameter of a bottom portion of the elastic body, 12.7 mm;

"E" indicates a radius of the elastic ring, 7.0 mm;

"F" indicates a thickness of the elastic ring, 0.5 mm;

"G" indicates a width of an interval space between the elastic ring and the elastic body at a connected portion, 0.5 mm;

"H" indicates a maximum width of an interval space between the elastic ring and the elastic body, 0.8 mm;

"i" indicates a horizontal length of a projected portion, 1.0 mm;

"J" indicates a width of the projected portion, 1.0 mm;

"K" indicates a vertical length of the projected portion, 2.0 mm;

"L" indicates a width of the connected portion, 2.0 mm;

"M" indicates a deviation of an central axis of the elastic ring from the elastic body, 0.15 mm;

"O" indicates a height of the elastic body, 8.0 mm;

"P" indicates a height of the elastic ring, 7.0 mm;

"Q" indicates a height of the flange, 0.8 mm;

"R" indicates a horizontal distance between the two opened ends of the elastic ring, 4.0 mm;

"S" indicates a vertical distance between the opened end and the top end of the elastic ring, 4.1 mm;

"T" indicates a width of a projected portion of the opened end of the elastic ring, 3.9 mm;

"U" indicates a length of the projected portion of the opened end of the elastic ring, 4.0 mm; and "W" indicates a width of a projected portion of the other opened end of the elastic ring, 3.9 mm.

In this example, furthermore, surfaces of each part of the device were smeared with silicone oil for avoiding adhesion of blood on these surfaces.

The above device and commercially obtainable glass tubes (10 ml vol., 13.6 mm I.D., Venoject evacuated blood-sampling tube; code No. VT-100P, Termo Co., Ltd.) as shown in FIG. 8a was used in the centrifugation procedure as described in the example 1. The isolated serum fraction was subjected to chemical analysis by means of the automatic blood analyzer. The blood separating device according to the present invention does not affect the results of the blood test (data not shown).

Example 3

The serum separating apparatus according to the present invention comprising an elastic body 21, an elastic ring 22 and a ball 23 was manufactured as described in Example 2 and as shown in FIGS. 5 and 6, except that a combination of the elastic body 21 and the elastic ring 22 weighs 0.402 g and their dimensions are follows:

A=11.5 mm; B=10.00 mm; C=9.8 mm; D=12.5 mm; E=7.0 mm; F=0.5 mm; G=0.5 mm; H=1.0 mm; i=1.0 mm; J=1.0 mm; K=2.0 mm; L=2.0 mm; M=0.25 mm; O=8.0 mm; P=7.0 mm; Q=0.8 mm; R=4.0 mm; S=4.1 mm; T=3.9 mm; U=4.0 mm; and W=3.9 mm.

In this example, furthermore, surfaces of each part of the apparatus 20 were smeared with silicone oil for avoiding adhesion of blood on these surfaces.

Figure 8B:
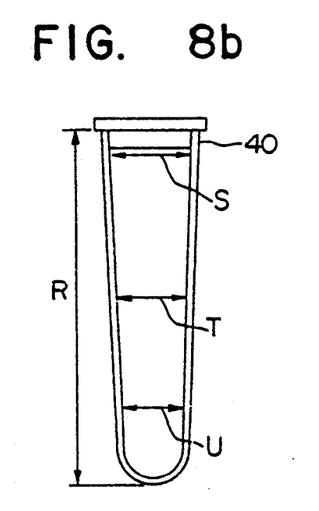
FIG. 8b is a side elevational view of a plastic tube used in the present invention, it being broken away for clearness.

All of the tubes used in this example were commercially obtainable polypropylene tubes (10 ml vol., Spitz type polypropylene tube, code No. EK-3401, Eiken Kizai Co., Ltd.) as indicated in FIG. 8b. In this figure, symbols "R", "S", "T" and "U" indicate each size of different portions of the tube 40. That is, "R" indicates a length of the tube, 97 mm; "S" indicates a diameter at a portion of 8 mm under from the top end of the tube, 14.0 mm; "T" indicates a diameter at a portion of 40 mm under from the top end of the tube, 13.5 mm; and "U" indicates a diameter at a portion of 65 mm under from the top end of the tube, 13.0 mm.

In the case of that a sample of blood is collected in the above spitz tube, a boundary of a clot fraction and a serum fraction of the centrifuged sample may be located at the midway between the portions indicated by "S" and "U". It is unusual that the boundary is located at the portion under the portion "U". Therefore, it can be observed that the inner diameter of the tube varies from 13 to 14 mm.

The elastic body is closely surrounded by the elastic ring to provide a gap between them. The width of this gap varies from about 1.0 mm to 0 mm according to portions thereof. As shown in FIG. 5, a part of the circular elastic body at 1.0 mm width portion of the gap is removed to form the body as a band having step-wedged ends. These ends is responsible for changing the diameter of the elastic body when it is subjected by a force applied from the outside, and resulting that an outer diameter of the body varies from 13 to 14 mm.

Also, the elastic body has three projections at an edge of the upper side of the opening to obstruct the pass of the ball through the opening.

Furthermore, the elastic body is formed so as to have 10 mm of the inner diameter, while the ball diameter is 9.8 mm, and thus the ball is easily trapped within the elastic body.

The centrifugation procedure using the above apparatus was performed as described in the example 1. The isolated serum fraction was subjected to chemical analysis by means of the automatic blood analyzer. The results indicated that the blood separating apparatus of this example does not affect the results of the tests (data not shown).

What is claimed is:

1. A serum separating apparatus used for separating serum and clot fractions in a step of centrifuging to blood sample, said serum separating apparatus comprising:
   an elastic ring have a specific gravity of between 1.05 and 1.5:
   an elastic cylindrical tube being flexible and having top and bottom elastic flanges, the top and bottom flanges extending horizontally from the surface of said tube and having a specific gravity of between 1.05 and 1.5, said elastic cylindrical tube being surrounded by said elastic ring; and
   a ball having a diameter in the range of 50 to 90% of the inner diameter of said tube and having a specific gravity less than 1.03, which is fitted to an opening of said elastic cylindrical tube, wherein
   the specific gravity of said ball is less than that of serum, and the mean specific gravity of said elastic tube, said elastic ring, and said ball is in the range between that of serum and clot.

2. A serum separating apparatus according to claim 1, wherein said elastic tube is made from a non-thrombotic and biologically inactive material, the non-thrombotic and biologically inactive material having the characteristic of preventing the blood sample from adhering thereto, wherein said material is selected from a group consisting of ABS resin, polyethylene terephtalate resin, polybutylene terephtalate resin, polycarbonate resin, polyamide resin, polymethylmethacrylate resin, and polyacetal resin, and wherein said ball is made of a plastic material selected from a group consisting of polystyrene and polypropylene.

3. A serum separating apparatus according to claim 1, wherein said elastic ring has an opening providing two horizontal ends.

4. A serum separating apparatus according to claim 3, wherein said two horizontal ends of the elastic ring respectively have an L-shape and a complementary reversed L-shape so as to interlock when meeting each other.

5. A serum separating apparatus according to claim 1, wherein said elastic ring has greater flexibility than said elastic tube.

6. A serum separating apparatus according to claim 5, wherein said elastic ring is made from one of derivatives of plant material including cellulose fibers and derivatives of animal material including silk fibers.

7. A serum separating apparatus used for dividing serum and clot fractions in a step of centrifuging a blood sample, said serum separating apparatus comprising:
   an elastic ring have a specific gravity of between 1.03 and 1.5:
   an elastic cylindrical tube having top and bottom elastic flanges, the top and bottom flanges extending horizontally from the surface of said elastic tube and having a specific gravity of between 1.03 and 1.5, the elastic tube being surrounded by said elastic ring; and
   a ball having a diameter in the range of at least 35% of the inner diameter of said tube and having a specific gravity which is less than 1.05, which is fitted to an opening of said elastic tube;
   wherein said elastic ring has two horizontal ends.

8. A serum separating apparatus according to claim 7, wherein said two horizontal ends of the elastic ring respectively have an L-shaped and a complementary reversed L-shape so as to interlock when meeting each other.

9. A serum separating apparatus according to claim 7, wherein said elastic tube and said elastic ring are made of a non-thrombotic and biologically inactive material, the non-thrombotic and biologically inactive material having the characteristic of preventing the blood sample from adhering thereto, wherein said material is selected from a group consisting of ABS resin, polyethylene terephtalate resin, polyurethane resin, polybutylene terephtalate resin, polycarbonate resin, polyamide resin, polymethylmethacrylate resin, and polyacetal resin, and wherein said ball is made of a plastic material selected from a group consisting of polystyrene and polypropylene.

10. A serum separating apparatus according to claim 7, wherein said elastic tube has an opening through one end to another with a gradient of inner diameters along the longitudinal axis of said tube.

11. A serum separating apparatus according to claim 10, wherein an upper end of said opening is widely opened to prevent accumulation of clot or platelet adhesion on said elastic body.

12. A serum separating apparatus used for dividing serum and clot fractions in a step of centrifuging a blood sample, said serum separating apparatus comprising:
   an elastic ring have a specific gravity of between 1.03 and 1.5:
   an elastic cylindrical tube having a specific gravity of between 1.03 and 1.5, the elastic ring surrounding said elastic cylindrical tube which is provided within an inner space, the elastic cylindrical tube having a supporting entity so as to be fixed with the elastic ring; and
   a ball having a specific gravity less than 1.05 and a diameter in the range 35% or more of the inner diameter of said tube;
   wherein an upper inner side of said elastic cylindrical tube has at least a pair of projected portions capable of being horizontally extended from said elastic tube so as to prevent passing of the ball through the tube.

13. A serum separating apparatus according to claim 12, wherein the bottom of the elastic body has an elastic flange which being horizontally extended to support the elastic ring.

14. A serum separating apparatus according to claim 12, wherein said elastic ring is an opened ring having first and second horizontal ends.

15. A serum separating apparatus according to claim 12, wherein said first and second horizontal ends are L-shape and reversed L-shape, respectively, so as to meet each other.

16. A serum separating apparatus according to claim 12, wherein said elastic body and said elastic ring are made of a non-thrombotic and biologically inactive material, which are difficult to be adhered by the blood sample, wherein said material is selected from a group consisting of ABS resin, polyethylene terephtalate resin, polyurethane resin, polybuthylene terephtalate resin, polycarbonate resin, polyamide resin, polymethylmethacrylate resin and polyacetal resin, and wherein said ball is made of a material selected from a group of plastic materials such as polystyrene and polypropylene.

17. A serum separating apparatus used for separating serum and clot fractions during centrifugation of a blood sample, said serum separating apparatus comprising:
   an elastic ring having a specific gravity of between 1.03 and 1.5:
   an elastic cylindrical tube having a specific gravity of between 1.03 and 1.5, surrounded by said elastic ring, said elastic cylindrical tube having top and bottom elastic flanges capable of horizontally extending from the surface of said elastic tube; and
   a ball having a diameter in the range of 50% to 90% of the inner diameter of said elastic tube, said ball being fit within an opening of said elastic body, wherein the specific gravity of said ball is less than 1.03, and the mean specific gravity of said elastic tube, said elastic ring, and said ball is in the range of between 1.03 and 1.08.

18. A serum separating apparatus used for separating serum and clot fractions during centrifugation of a blood sample, said serum separating apparatus comprising;
   an elastic ring having a specific gravity of between 1.05 and 1.5;
   an elastic cylindrical tube having top and bottom elastic flanges extending horizontally from the surface of said elastic tube, the elastic tube having a specific gravity of between 1.05 and 1.5, the elastic ring surrounding at least a portion of the elastic tube; and
   a ball having a diameter int he range of 50% to 90% of the inner diameter of said elastic tube and having a specific gravity which is at most equal to 1.03, the ball being fit to an opening of said elastic tube,
   wherein said elastic material used for the elastic ring is more flexible than the material used for the elastic tube.

19. A serum separating apparatus according to claim 18, wherein the material used for the elastic ring is one of plant material including cellulose fibers and animal material including silk fibers.

* * * * *

UNITED STATES PATENT AND TRADEMARK OFFICE
CERTIFICATE OF CORRECTION

PATENT NO. : 5,266,199

DATED : November 30, 1993

INVENTOR(S) : Tsukagoshi et al.

It is certified that error appears in the above-identified patent and that said Letters Patent is hereby corrected as shown below:

| | | |
|---|---|---|
| In Column 1, Line 41, | delete "come", and insert --comes--. |
| In Column 5, Line 5, | delete "FIG." and insert --FIGS.--. |
| In Column 6, Line 63, | delete "BT and insert --VT--. |
| In Column 7, Line 26, | delete "Sisakusyo" and insert --Seisakusyo--. |
| In Column 7, Line 44, | delete "T.Bil" and insert --"T·Bil--. |
| In Column 7, Line 44, | delete "D.bil" and insert --"D·bil"--. |
| In Column 7, Line 48, | delete "+" and insert --"+"--. |
| In Column 9, Line 66, | delete "FIG." and insert --FIGS.--. |

UNITED STATES PATENT AND TRADEMARK OFFICE
CERTIFICATE OF CORRECTION

PATENT NO. : 5,266,199

DATED : November 30, 1993

INVENTOR(S) : Tsukagoshi et al.

It is certified that error appears in the above-identified patent and that said Letters Patent is hereby corrected as shown below:

In Column 11, Line 3, delete "B=10.00" and insert --B=10.0--.

In Column 14, Line 36, delete "int he" and insert --in the--.

Signed and Sealed this

Seventh Day of June, 1994

Attest:

BRUCE LEHMAN

Attesting Officer     Commissioner of Patents and Trademarks